(12) United States Patent
Underwood et al.

(10) Patent No.: US 12,370,356 B2
(45) Date of Patent: Jul. 29, 2025

(54) PRECISION ROLLER CLAMP ASSEMBLY

(71) Applicant: CareFusion 303, Inc., San Diego, CA (US)

(72) Inventors: Wesley Underwood, Anaheim, CA (US); Luca Nasi, Spilamberto (IT); Mum Pew Ng, Singapore (SG); Aaron E Wang, Laguna Hills, CA (US); Corey M. Christensen, Anaheim, CA (US)

(73) Assignee: CareFusion 303, Inc., San Diego, CA (US)

( * ) Notice: Subject to any disclaimer, the term of this patent is extended or adjusted under 35 U.S.C. 154(b) by 1 day.

(21) Appl. No.: 18/118,512

(22) Filed: Mar. 7, 2023

(65) Prior Publication Data

US 2023/0285736 A1 Sep. 14, 2023

Related U.S. Application Data

(60) Provisional application No. 63/319,444, filed on Mar. 14, 2022.

(51) Int. Cl.
*A61M 39/28* (2006.01)
*A61M 5/168* (2006.01)

(52) U.S. Cl.
CPC ...... *A61M 39/286* (2013.01); *A61M 5/16813* (2013.01); *A61M 5/16881* (2013.01)

(58) Field of Classification Search
CPC .................................................. A61M 39/286
See application file for complete search history.

(56) References Cited

U.S. PATENT DOCUMENTS

| 4,013,263 | A | * | 3/1977 | Adelberg | A61M 39/286 251/6 |
| 4,047,694 | A | * | 9/1977 | Adelberg | A61M 39/286 251/6 |
| 4,340,201 | A | * | 7/1982 | Becker, Jr. | A61M 39/286 251/6 |
| RE31,584 | E | * | 5/1984 | Adelberg | A61M 39/286 251/6 |
| 5,014,962 | A | * | 5/1991 | Adelberg | A61M 39/286 251/6 |
| 6,129,330 | A | * | 10/2000 | Guala | A61M 39/286 251/6 |

(Continued)

FOREIGN PATENT DOCUMENTS

| EP | 0239718 A2 | 10/1987 |
| EP | 0985425 A2 | 3/2000 |
| EP | 1452202 A1 | 9/2004 |

OTHER PUBLICATIONS

International Search Report and Written Opinion for Application No. PCT/US2023/014379, dated May 30, 2023, 17 pages.

*Primary Examiner* — Robert K Arundale

(57) ABSTRACT

A precision roller clamp assembly for adjusting the fluid flow rate in a tube of an infusion set is provided. The roller clamp assembly includes a housing to receive the tube and a roller wheel moveably engaged with the housing. The housing includes a tube groove disposed in a guide wall, the tube groove dimensions configured to provide a precise fluid flow adjustment over a majority of the travel path of the roller wheel. A method of operating a precision roller clamp assembly is also provided.

14 Claims, 9 Drawing Sheets

(56) References Cited

U.S. PATENT DOCUMENTS

| | | | | |
|---|---|---|---|---|
| 6,929,236 B1* | 8/2005 | Height | ................ | A61M 39/286 |
| | | | | 137/553 |
| 2008/0083890 A1* | 4/2008 | Adelberg | ................ | F16K 7/066 |
| | | | | 251/6 |
| 2009/0247964 A1* | 10/2009 | Kitani | ................... | A61M 39/28 |
| | | | | 604/250 |

* cited by examiner

PRECISION ROLLER CLAMP ASSEMBLY

CROSS REFERENCE TO RELATED APPLICATION

This application claims the benefit of priority under 35 U.S.C. § 119 to U.S. Provisional Patent Application Ser. No. 63/319,444, entitled "Precision Roller Clamp Assembly, filed on Mar. 14, 2022, the entire contents of which is incorporated herein by reference.

TECHNICAL FIELD

The present disclosure generally relates to a gravity intravenous (IV) set or infusion pump flow control device, and in particular a precision roller clamp assembly.

BACKGROUND

During administration of infusion therapy via gravity IV set, a roller clamp is often used to control the flow rate of the infusion. A roller clamp is composed of a body that constrains the IV tubing under a wheel. As the user moves the roller clamp wheel from the top of the roller clamp body to the bottom, the tubing becomes progressively squeezed within a slot or channel of the roller clamp body. The squeezing action of the tubing between the roller clamp body and wheel causes the inner diameter of the tubing to decrease as the wheel travels down the length of the roller clamp body. The gradual decrease in the inner diameter of the tubing as the roller wheel travels down the roller clamp body causes a similar decrease in flow rate, allowing clinicians to control the flow of the infusate by moving the wheel up or down along the body of the roller clamp. The roller clamp is also responsible for fully stopping infusate flow and stopping flow during instances of pressure increases such as when a syringe bolus is delivered downstream of the roller clamp or when the IV set is changed to a new IV bag.

Clinicians most often set sustained infusion rates controlled by roller clamps to a range of flow rates from around 250 mL/hr to 25 mL/hr. Flow rates faster than 250 mL/hr to full open flow are not used as often to deliver sustained medication delivery.

Current roller clamps often constrain the total travel length of the wheel to set flow rates from around 250 to around 25 mL/hr to a distance of around 7 mm at most on average, while the rest of the distance that the wheel may travel does not coincide with a flow rate between around 250 mL/hr and around 25 mL/hr. A distance of 7 mm is a rather small window to efficiently and easily titrate the infusion. This provides a limited range of flow rate control because the roller wheel is essentially too sensitive in that a small movement of the roller wheel or dimension change causes a large change in flow rate of the fluid through the tube. Thus, the relatively course flow rate change provided by a typical roller clamp makes it difficult to provide precise flow control.

Also, typical roller clamps have flow rate drifting issues or lack of flow stability based on stress relaxation caused by the tubing being in a compressed state between the roller clamp body and wheel, where the constricted fluid orifice responsible for set flow rate changes diameter, thus changing the flow rate over time.

Further, typical roller clamps may reach their fully occluded state while the wheel is still half way along the roller body so that to a clinician inspecting the patient medication, the described wheel position is ambiguous. For example, the previous clinician may have intended to fully occlude the tubing and didn't ensure that the wheel was fully in the down position, or an amount of medication was intended to be delivered but the flow rate drifted to off over time. Without appropriate wheel position with respect to the body, the clinician must check the patient chart to understand these metrics.

Also, another issue is the force required to move the wheel along the roller clamp body. It has been found that if the force is above 20 N, the wheel is too difficult to manipulate. Repeated use of a roller clamp with too high of a movement force may cause soreness in the pad of the clinician's thumb. In addition, if the hands of the clinician are slickened by fluids, there may not be enough friction available to allow movement of the wheel to provide medication control.

Thus, it is desirable to provide a precision roller wheel assembly that provides quick top end flow rate adjustments, provides increased fine flow rate adjustments within a clinically relevant high and low flow rate range, provides increased roller wheel distance between a clinically relevant low flow rate to a fully occluded range, eliminates or minimizes positive change in flow rate over time, provides full occlusion only at the end of the roller wheel travel path, and limits the force required to move the roller wheel down the body of the roller clamp.

SUMMARY

One or more embodiments provide a roller clamp assembly. The roller clamp assembly includes a housing configured to receive a portion of a tube of an infusion set. The housing includes two opposing side walls spaced apart from each other, each side wall having an opposing guide groove longitudinally positioned in an interior surface, a guide wall disposed between the side walls and a tube groove disposed within the guide wall. The roller clamp assembly also includes a roller wheel having two axial projections slidingly seated in the guide grooves, the roller configured to move along a longitudinal axis of the housing over a movement range as the projections slide in the guide grooves.

One or more embodiments provide a method of operating a roller clamp assembly. The method includes inserting a tube of an infusion set into a precision roller clamp assembly comprising a housing having two opposing side walls spaced apart from each other, each side wall having an opposing guide groove longitudinally positioned in an interior surface, a guide wall disposed between the side walls and a tube groove disposed within the guide wall, and a roller wheel having two axial projections slidingly seated in the guide grooves. The method also includes moving the roller wheel through a first travel range of the guide groove to engage the tube to cause a flow rate of fluid through the tube to go from a fully open flow rate to a clinically determined high flow rate. The method further includes moving the roller wheel to a position in a second travel range of the guide groove to increasingly impinge the tube to cause a desired flow rate of fluid through the tube between the clinically determined high flow rate and a clinically determined low flow rate.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
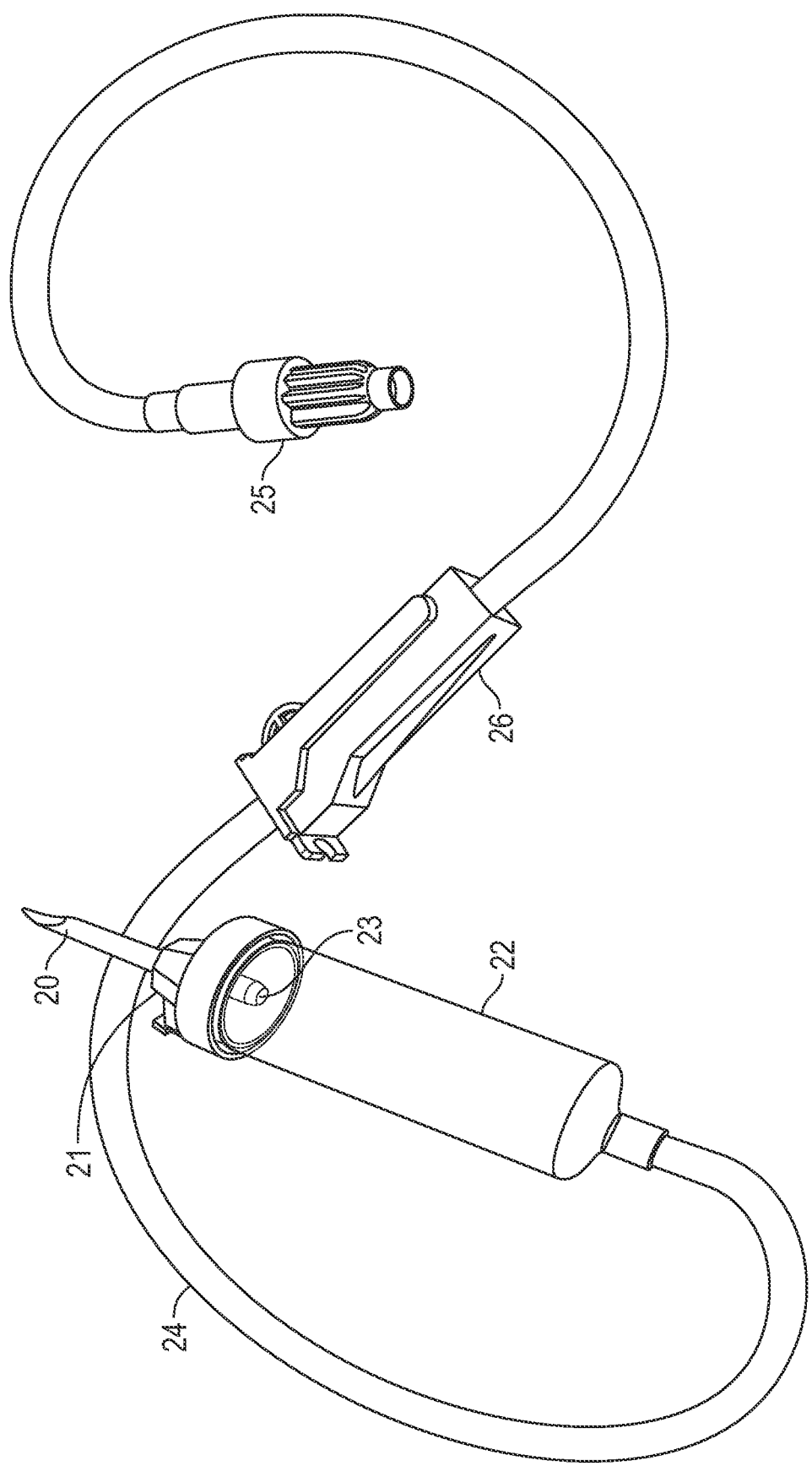
FIG. 1 depicts a perspective view of an example infusion set having a typical roller clamp.

The present disclosure relates to a roller clamp and in particular to a roller clamp for use in gravity administration sets, pump sets, secondary sets, or any other sets that may use a roller clamp to regulate the flow of an infusion. The roller clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drop chamber 22. The vent 21 may be provided with a bacterial filter to prevent bacteria from entering the equipment.

The drop chamber 22 has a drop generator 23 at the top of the drop chamber 22 that produces drops of a certain size. Drops from the drop generator 23 fall into the drop chamber 22 such that the drop chamber 22 is partially filled with fluid or liquid. This prevents air bubbles from entering the connector tube 24, which would be harmful to a patient. A particle filter may be provided at the lower aperture of the drop chamber 22.

The connector tube 24 connects the drop chamber 22 with the patient. The connector tube 24 is usually around 150 cm long and can be manufactured from PVC. The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into the circulatory system of a patient (e.g., into a vein).

Between the drop chamber 22 and the Luer fitting 25 and engaging with the connector tube 24, is a roller clamp 26. The present disclosure is concerned with an improved roller clamp assembly, but a typical roller clamp 26 as known in the art will now be described for background information.

Figure 2:
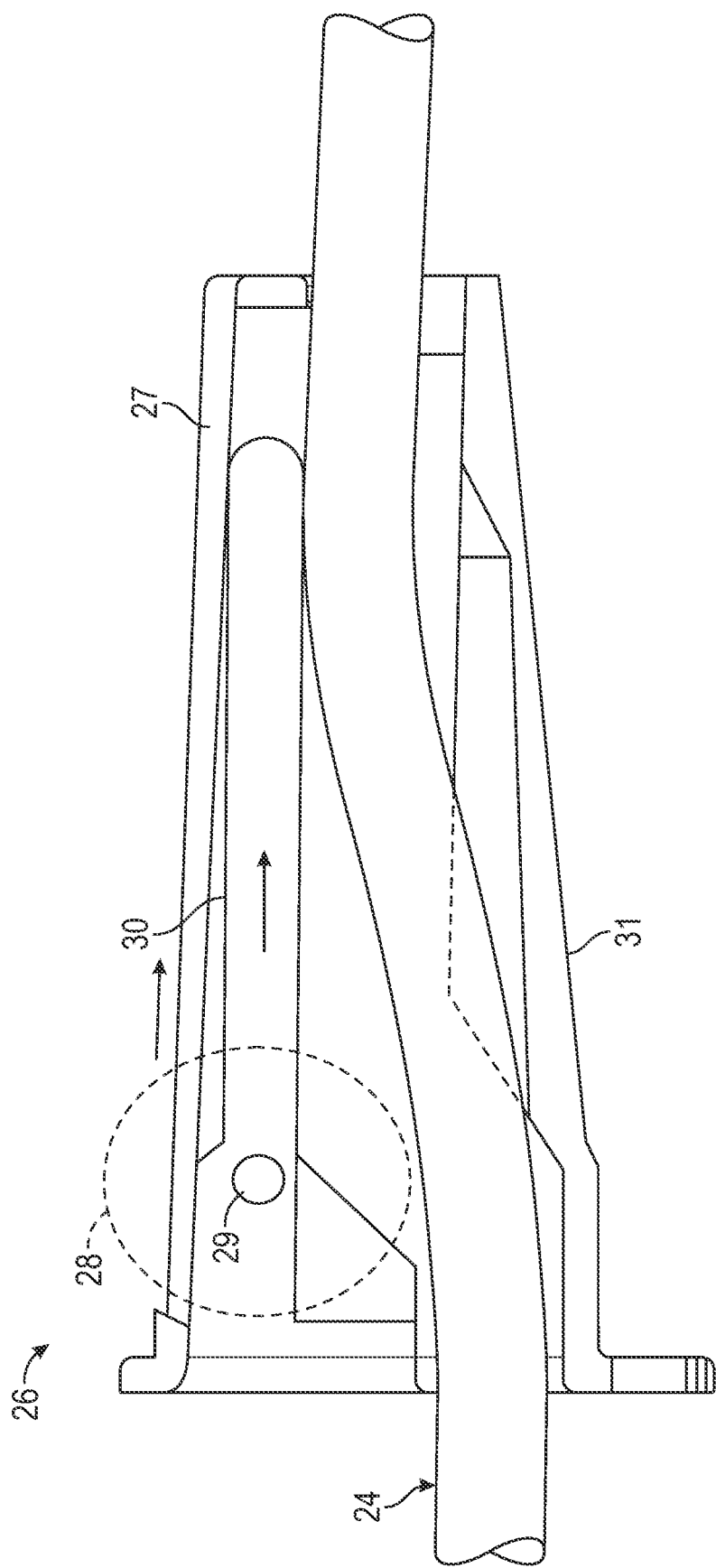
FIG. 2 depicts a cross-section side view of the roller clamp of FIG. 1.

The roller clamp 26 illustrated in FIG. 2 has a housing 32 with two opposing side walls 27 having a pair of guide grooves 30 that are aligned with each other and face each other. A flow-regulating roller wheel 28 is provided having axially-projecting shafts 29 protruding from the centers of each side of the roller wheel 28. The roller wheel 28 is shown in outline for clarity. The shafts 29 of the roller 28 are captured by and seated in the guide grooves 30 so that the roller wheel 28 can move up and down the guide grooves 30 along the housing 32 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller wheel 28 and a guide wall 31 that is opposed to the roller wheel 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller wheel 28.

Thus, rolling the roller wheel 28 downwardly along the guide grooves 30 in the direction of the gradually closer guide wall 31 in the direction of the arrows causes the roller wheel 28 to impinge against the connector tube 24. As the roller wheel 28 impinges on the tube 24, the tube 24 becomes squeezed, as it is a flexible material such as PVC, and the lumen of the infusion tube 24 therefore becomes smaller. In this way, by narrowing of the lumen, the flow rate of fluid passing through the connector tube 24 can be regulated.

Thus, the roller clamp 26 controls the flow rate through the infusion tube 24 by clamping the infusion tube 24 between the roller wheel 28 and the guide wall 31. As discussed above, this provides for a course flow rate change because a small movement of the roller wheel 28 causes a large change in the flow rate of the fluid through the tube 24. Also, the force of the fluid in the tube 24 exerts a biasing force against the roller wheel 28, which often leads to slippage of the wheel roller 28 (e.g., the roller wheel 28 rolls back) from the adjusted position.

Figure 3:
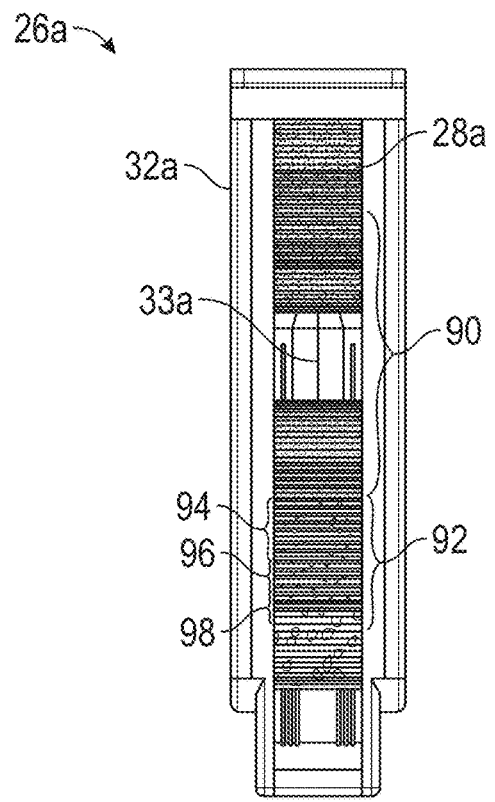
FIG. 3 depicts a top view of a typical roller clamp showing roller wheel positioning for various flow rates.
Figure 4:
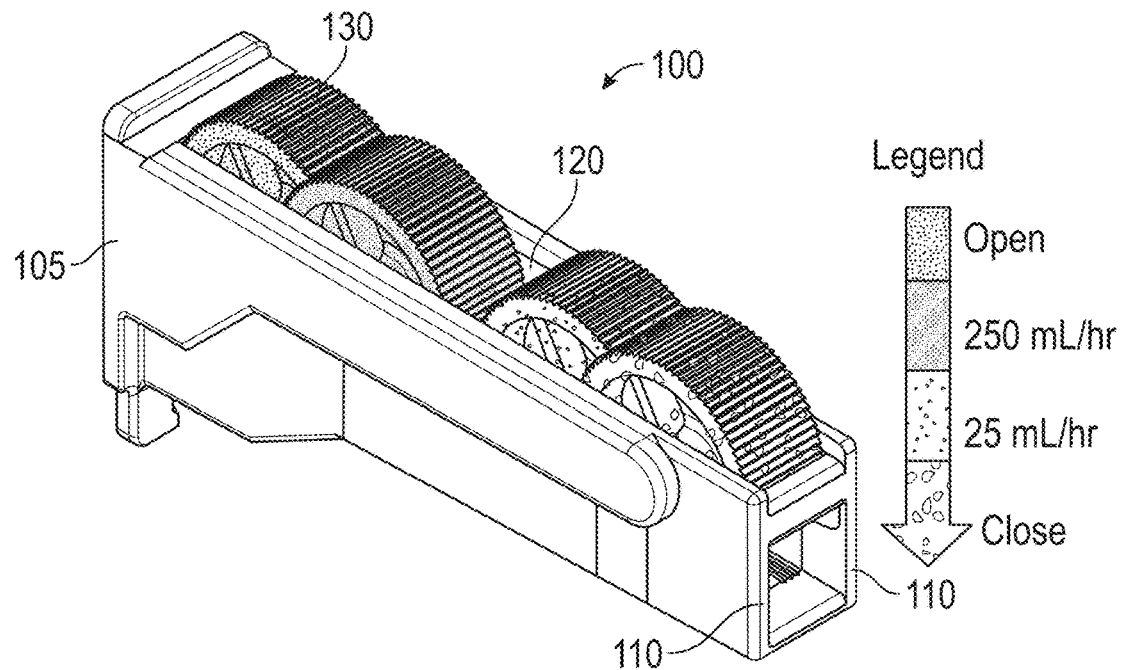
FIG. 4 depicts a perspective view of a precision roller clamp assembly showing roller wheel positioning for various flow rates, according to aspects of the disclosure.

As shown in FIG. 3, a typical roller clamp 26a has a housing 32a with a tube groove 33a having a groove geometry with one constant groove draft angle (e.g., linear) and a roller wheel 28a that travels over the tube groove 33a along the housing 32a on a linear path. The relationship between fluid orifice diameter and flow rate is non-linear, especially in the flow rates that are clinically relevant. When graphing typical roller wheel position versus flow rate, the plot is non linear, indicating the requirement of large movements of the roller wheel to gain clinical control of the flow rate and small movements of the roller wheel to control flow rate during the clinically relevant flow rate range.

As also shown in FIG. 3, the roller wheel 28a travel range 90 between a fully open flow and a 250 mL/hr flow rate takes up the majority of the travel path of the roller wheel 28a in the housing 32a, while the roller wheel 28a travel range 92 for the desired flow rate range (e.g., clinically relevant flow rate range) between 250 mL/hr and 25 mL/hr is much smaller (e.g., 7.05 mm). The travel range 92 has subset ranges, such as travel range 94 (e.g., 4.24 mm) for flow rates between 250 mL/hr and 100 mL/hr, travel range 96 (e.g., 1.50 mm) for flow rates between 100 mL/hr and 60 mL/hr, and travel range 98 (e.g., 1.31 mm) for flow rates between 60 mL/hr and 25 mL/hr. Due to the large travel range 90, the majority of the roller wheel 28a movement in the housing 32a does not yield clinically relevant flow rates.

As discussed above, current roller clamps often constrain the total travel length of the wheel to set flow rates from around 250 to around 25 mL/hr to a distance of around 7 mm at most on average, while the rest of the distance that the wheel may travel does not coincide with a flow rate between around 250 mL/hr and around 25 mL/hr. A distance of 7 mm is a rather small window to efficiently and easily titrate the infusion.

In aspects of the disclosure, a precision roller clamp assembly divides the distance that the wheel travels across the roller clamp body into at least three regions to increase the usability of the roller clamp. The first region, near the top of the roller clamp body and down to around 25% of the total distance that the wheel may travel, adjusts flow rate from full open flow to around 250 mL/hr. The second region, from the prior 25% to around 75% of the total distance that the wheel may travel, adjusts flow rate from around 250 mL/hr to around 25 mL/hr. The third region, from the prior 75% to around 100% of the total distance that the wheel may travel, adjusts flow rate from around 25 mL/hr to full flow rate stop and tubing occlusion.

In addition to the importance of a roller clamp having adequate wheel adjustability within ranges of clinically relevant flow rates, flow stability (e.g., the rate at which the flow rate changes after the roller clamp flow rate is set) is also important. Ideally, after the flow rate is set the flow rate is stable and stays the same. For example, some medications may have issues if they are infused too fast, such as due to the roller clamp flow rate drifting from a controlled flow rate too full open. A positive flow rate change over time is more of an issue than a negative flow rate change over time. Due to stress relaxation caused by the tubing being in a compressed state between the roller clamp body and wheel, the constricted fluid orifice responsible for set flow rate changes diameter, thus changing the flow rate over time.

In aspects of the disclosure, while it may not be possible to completely remove the effect of tubing stress relaxation and its associated change in flow rate, a precision roller clamp assembly provides that the amount of stress relaxation may be managed to ensure that the flow rate change is as close to zero as possible, and that the flow rate only slows with time if a change in flow rate does occur.

As discussed above, another issue is the human factors question associated with the roller clamp. Some current roller clamps may reach their fully occluded state while the wheel is still half way along the roller body. To a clinician inspecting the patient medication, the described wheel position is ambiguous. Did the previous clinician intend to fully occlude the tubing and didn't ensure that the wheel was fully in the down position? Was the medication intended to be delivered but the flow rate drifted to off over time? Without appropriate wheel position with respect to the body, the clinician must check the patient chart to know.

In aspects of the disclosure, a precision roller clamp assembly is provided that is intended to remove such ambiguity by ensuring that if the wheel position is not fully to the bottom of the roller body, the fluid flow is not intended to be stopped. In other words, the only time the fluid flow is intended to be fully occluded or stopped is when the roller wheel is at the end of the roller clamp body.

In aspects of the disclosure, a precision roller clamp assembly has a non linear groove geometry tuned to each of three flow control regions. The first region decreases the distance that the wheel must travel from full open flow rate until the flow rate reaches a clinically relevant high flow rate (e.g., 250 mL/hr). The second region increases the distance that the roller wheel may travel during titration within a clinically relevant high and low flow rate range (e.g., between 250 mL/hr and 25 mL/hr), allowing finer flow control. The third region increases the distance that the roller wheel may travel during titration within a clinically relevant low flow rate to fully occluded range (e.g., between 25 mL/hr and 0 mL/hr).

In aspects of the disclosure, because the flow rate is dependent on the diameter of the fluid orifice created by the squeezed tubing, the different flow control regions are achieved by managing the rate at which the fluid orifice is decreased for each region. For the first region, the groove geometry is angled so that the tubing inner diameter is squeezed quickly with a relatively small wheel travel distance. The groove geometry of the second flow control region is angled more gradually than the first region so that the wheel must travel a longer distance across the flow rate range. The groove geometry third flow control region is also uniquely angled so that the wheel must travel an appropriate distance to change the flow rate from a low rate to fully occluded. Thus, the groove geometry of the low flow to closure third region is tuned so that full occlusion is only possible when the roller wheel is positioned at the bottom of the roller clamp.

Regarding flow stability, typical roller clamps may exhibit both negative and positive flow rate change over time.

In aspects of the disclosure, a roller clamp assembly is provided where the groove geometry is tuned so that the tubing is appropriately constrained between the groove and wheel. Thus, when the tubing undergoes stress relaxation, the tubing inner diameter may only decrease into itself, resulting in only a negative flow rate change. In other words, the roller clamp assembly constrains the tubing directly under the wheel on all sides so that when the tubing does undergo stress relaxation, it may only relax into the void space of the fluid orifice. Thus, the roller clamp assembly minimizes positive change in flow rate over time, reducing the risk of faster medication delivery than intended.

The amount that the tubing is compressed between the body and the wheel is related to how much force is related to move the wheel across the tubing. Wall thickness and tubing durometer are also a factor as well as wheel diameter. Typical roller clamps exert an unnecessary amount of compression on the tubing, resulting in higher forces required to move the wheel.

In aspects of the disclosure, the force to move the wheel may be reduced by balancing the wheel diameter and tubing compression gap under the wheel and between the body. Thus, the disclosed roller clamp assembly limits the force required to move the roller wheel down the body of the roller clamp.

With reference to FIGS. 4-11, a precision roller clamp assembly 100 is shown. The roller clamp assembly 100 has a housing 105 having an open-ended boxlike construction and is dimensioned and configured to receive tubing, such as connector tube 24. Two opposing side walls 110 each have a guide groove 120 that are aligned with each other and face each other. A roller wheel 130 is provided having axially-projecting shafts 132 protruding from the centers of each side of the roller wheel 130. The shafts 132 of the roller wheel 130 are seated in the guide grooves 120 so that the roller wheel 130 can move up and down the guide grooves 120. A guide wall 112 is opposed to the roller wheel 130 and the surface of the guide wall 112 converges along its length toward the position of the guide grooves 120. A tube groove 133 is disposed in the guide wall 112, the tube groove 133 being non-linear. For example, the tube groove 133 may vary in width W and/or depth D along the length L of the tube groove 133.

In use, the tube 24 passes through the roller clamp assembly 100, between the two opposing side walls 110, the roller 130 and the guide wall 112 that is opposed to the roller 130. Rolling the roller 130 downwardly along the guide grooves 120 in the direction of the gradually closer guide wall 112 causes the roller 130 to impinge against the tube 24. As the roller 130 impinges on the tube 24, the tube 24 becomes squeezed against the tube groove 133 and the guide wall 112, as it is a flexible material such as PVC, and the lumen of the infusion tube 24 therefore becomes smaller. In this way, by narrowing of the lumen, the flow rate of fluid passing through the connector tube 24 can be regulated.

Figure 5:
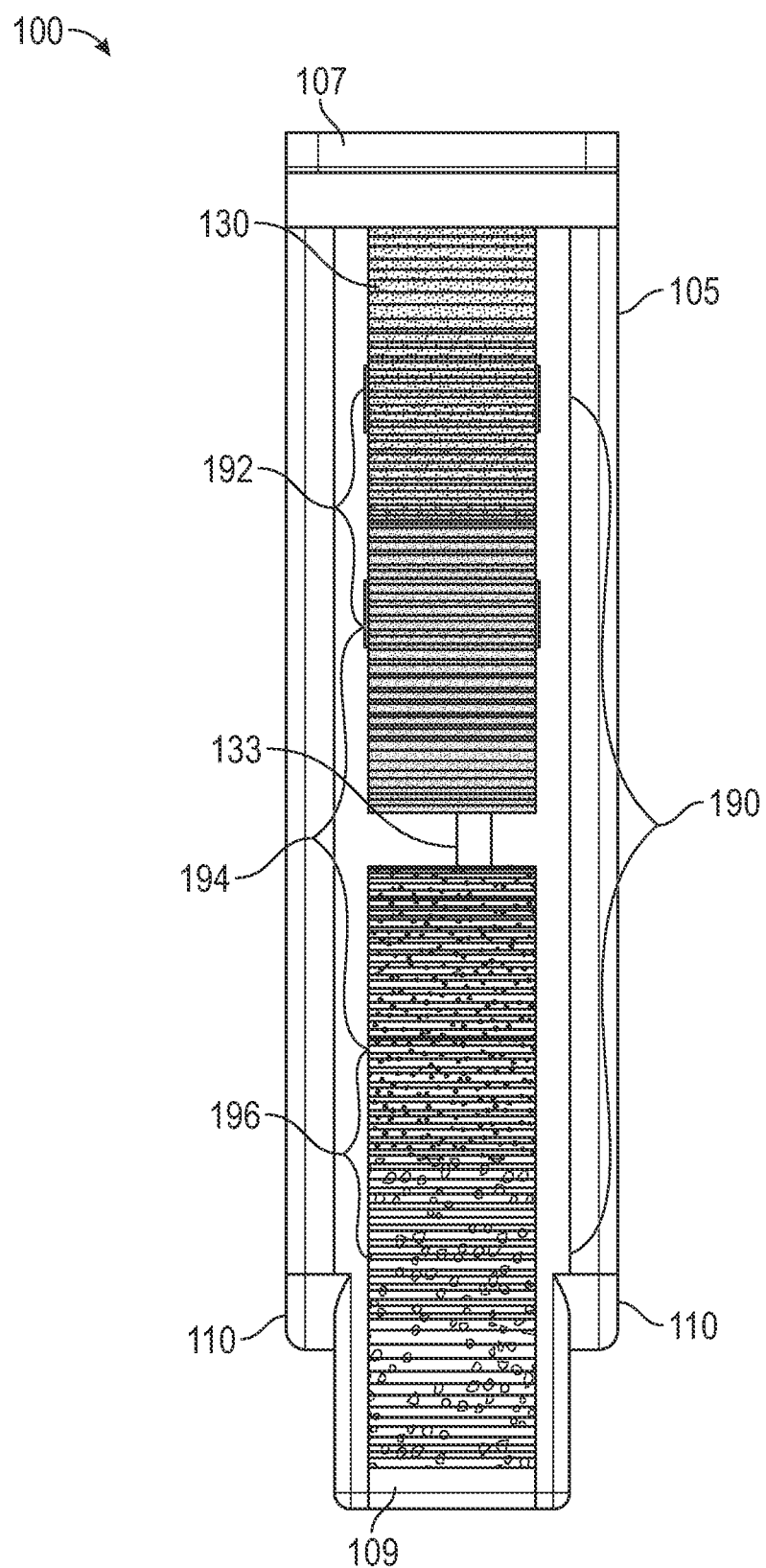
FIG. 5 depicts a top view of the precision roller clamp assembly of FIG. 4, according to aspects of the disclosure.

As shown in FIG. 5, the roller wheel 130 has a movement range 190 defined by the positions of the shafts 132 when the roller wheel 130 is at a first housing end 107 and when the roller wheel 130 is at a second housing end 109. As seen, a travel range 192 of the roller wheel 130 between a fully open flow and a 250 mL/hr flow rate takes up a small portion (e.g., ≤25%) of the movement range 190, as opposed to the much larger travel range 90 of roller clamp 26a shown in FIG. 3. In addition, a travel range 194 of the roller wheel 130 for the clinically relevant flow rate range between 250 mL/hr and 25 mL/hr is a much larger portion (e.g., ≥50%) of the movement range 190, as opposed to the much smaller travel range 92 of roller clamp 26a shown in FIG. 3. Similarly to the travel range 192, a travel range 196 of the roller wheel 130 between the lowest clinical flow rate (e.g., 25 mL/hr) and a fully closed flow rate takes up a similar size portion (e.g., ≤25%) of the movement range 190. Here, due to the large travel range 194, at least half of the roller wheel 130 movement in the housing 105 yields clinically relevant flow rates. This large travel range 194 provides for very granular and precise control over the flow rate within the clinically relevant flow rate range.

Figure 6:
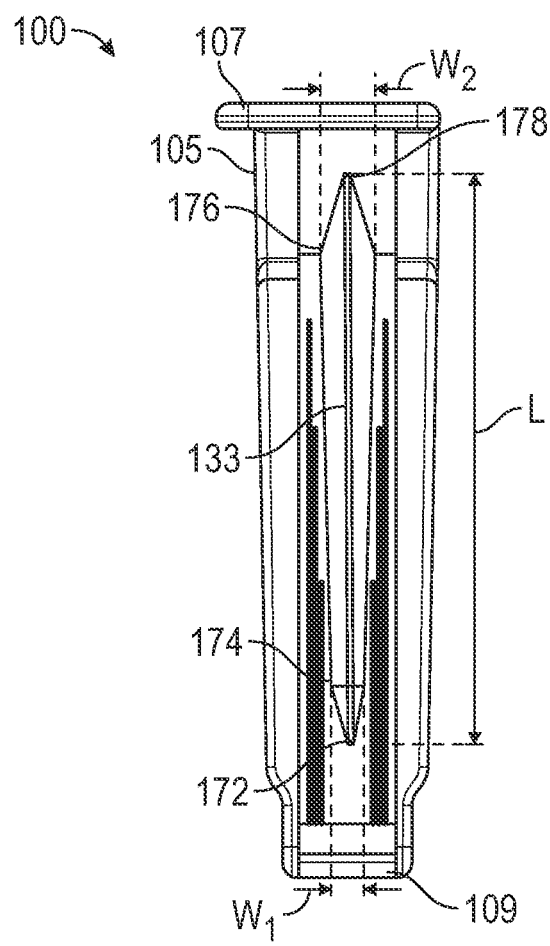
FIG. 6 depicts a top view of the precision roller clamp assembly of FIG. 4 with the roller wheel removed, according to aspects of the disclosure.
Figure 7:
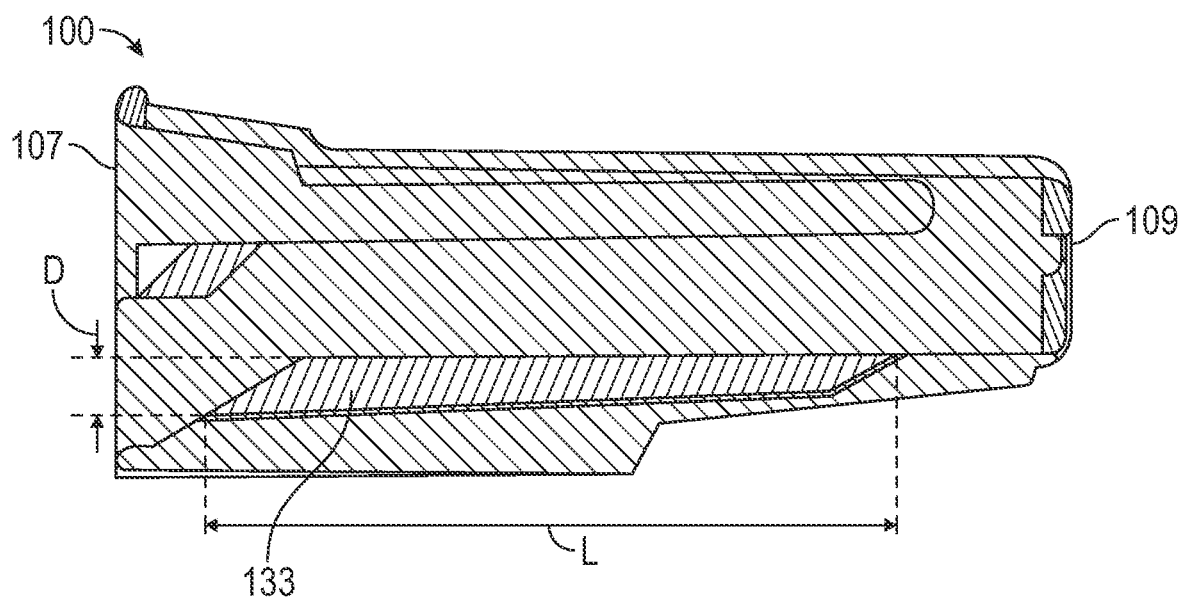
FIG. 7 depicts a cross-section side view of the precision roller clamp assembly of FIG. 6, according to aspects of the disclosure.
Figure 8:
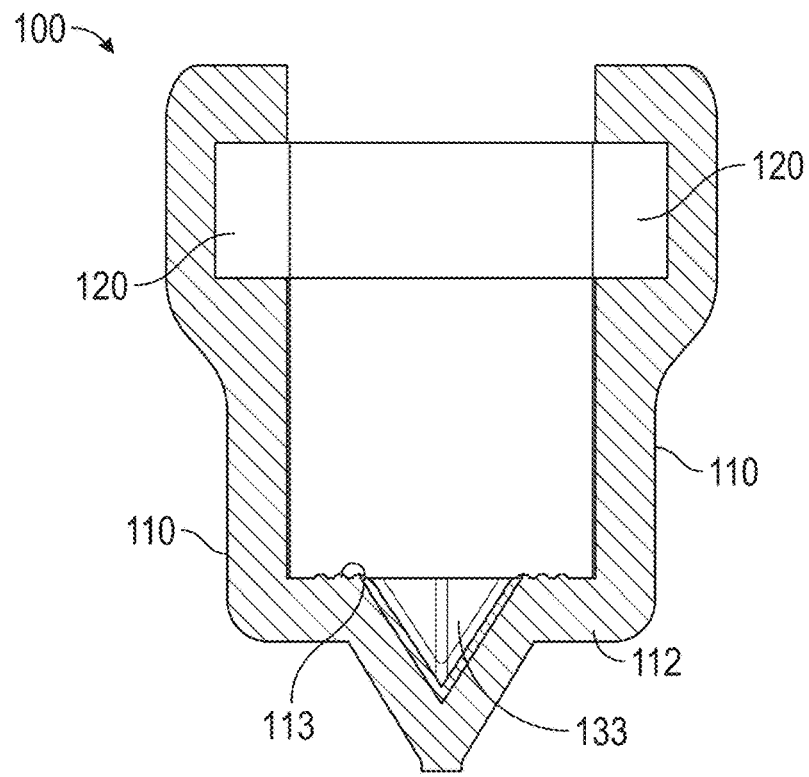
FIG. 8 depicts a cross-section front view of the precision roller clamp assembly of FIG. 6, according to aspects of the disclosure.

As shown in FIGS. 6 and 7, the tube groove 133 may vary in width W and/or depth D along the length L of the tube groove 133. For example, the width W may start at or near zero at an end 172 closest to the second housing end 109 and widen out to a width W1 at the transition point 174 between travel range 196 and travel range 194. The width W may steadily widen further to a widest width W2 at the transition point 176 between travel range 194 and travel range 192. The width W may then narrow back to zero or near zero at an end 178 closest to the first housing end 107. Accordingly, the steadily widening width from W1 to W2 of the tube groove 133 corresponds to the entirety of the movement range 190. Also, the width W steadily widens over the entire travel range 194, thus providing a large length of travel for the roller wheel 130 that corresponds to fine fluid flow adjustment.

Similarly, the depth D of the tube groove 133 may vary and become deeper going from the second housing end 109 to the first housing end 107. Thus, a varying depth D of the tube groove 133 may also correspond to the entirety of the travel range 194, again providing a large length of travel for the roller wheel 130 that corresponds to fine fluid flow adjustment. As shown, the tube groove 133 has a triangular or V shaped geometry, however the tube groove 133 may have any suitable geometry (e.g., semi-circular, square, rectangular, trapezoidal).

Figure 9:
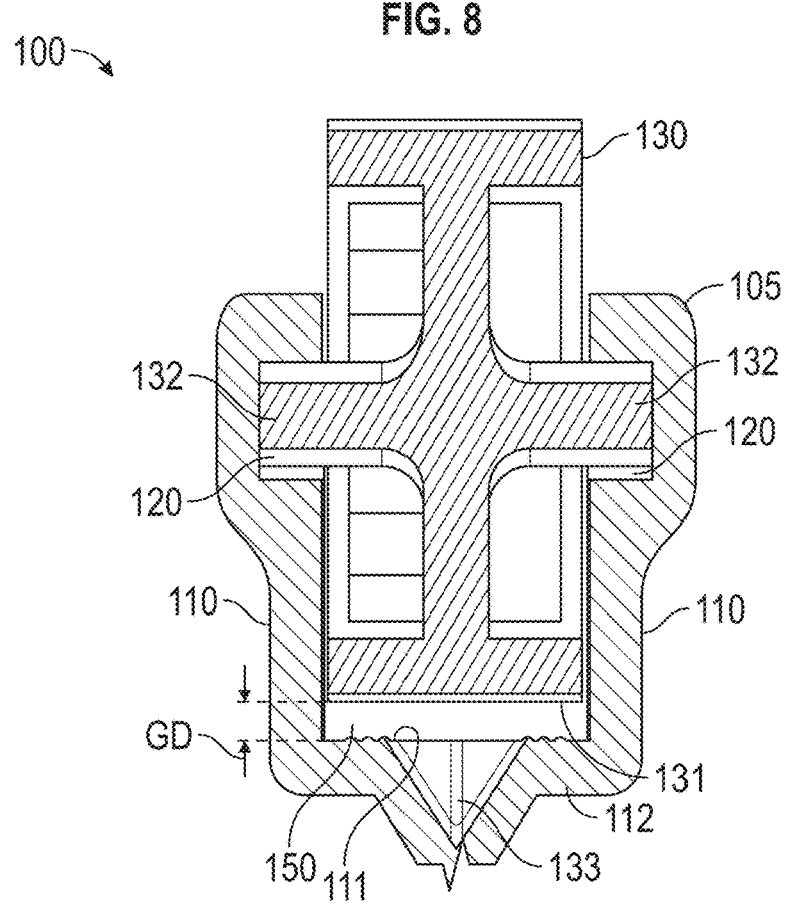
FIG. 9 depicts a cross-section front view of the precision roller clamp assembly of FIG. 4, according to aspects of the disclosure.

As shown in FIG. 9, a gap 150 is disposed between an outer perimeter 131 of the roller wheel 130 and an inner surface 111 of the guide wall 112. Here, the inner surface 111 of the guide wall 112 on each side of the tube groove 133 has protrusions 113 (e.g., ridges) extending towards the roller wheel 130 and/or into the gap 150 (see FIGS. 8 and 9). Similarly to the width W and the depth D of the tube groove 133, a gap distance GD of the gap 150 may vary along the length of the guide wall 112. For example, the gap distance GD may be smallest at the second housing end 109 and may be largest at the first housing end 107. Thus, a varying gap distance GD may also correspond to the entirety of the travel range 194, again providing a large length of travel for the roller wheel 130 that corresponds to fine fluid flow adjustment.

Figure 10:
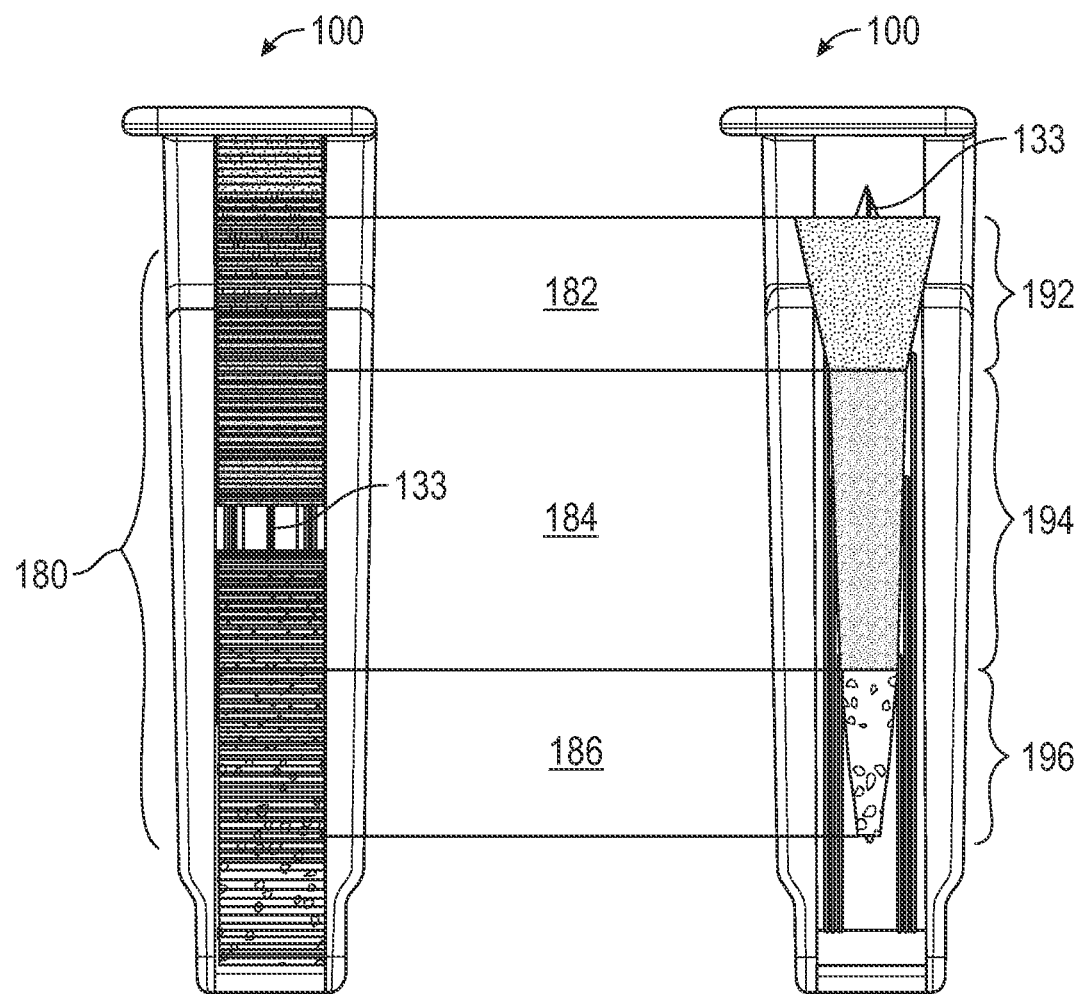
FIG. 10 depicts a top view of the precision roller clamp assembly of FIG. 4 highlighting specific flow regions, according to aspects of the disclosure.
Figure 11:
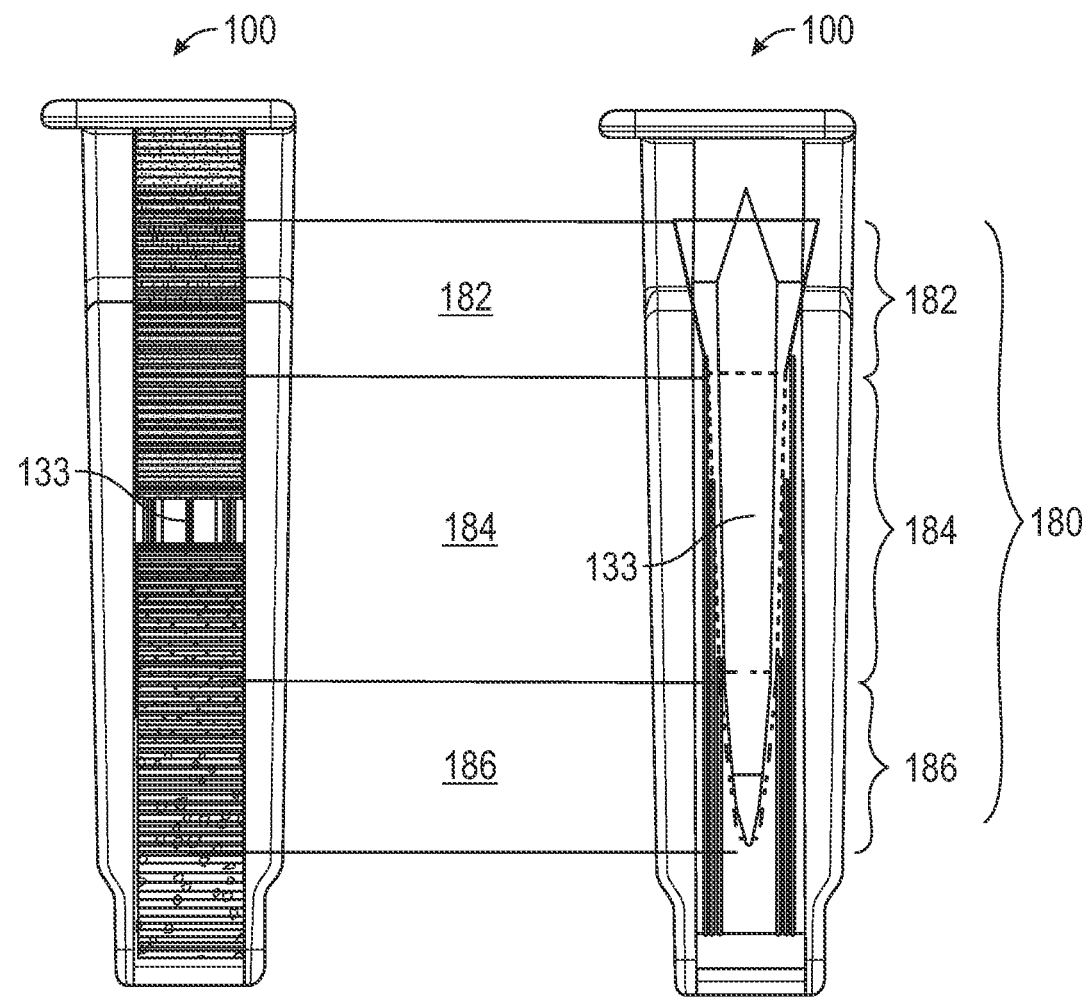
FIG. 11 depicts a top view of the precision roller clamp assembly of FIG. 4 highlighting specific flow regions, according to aspects of the disclosure.

As shown in FIGS. 10 and 11, the width W and the depth D of the tube groove 133, and the gap distance GD of the gap 150 may each be tuned to create a flow profile 180 having specific flow regions 182, 184, 186. Here, the flow region 182 may be configured as a full open region that corresponds to travel range 192 of the roller wheel 130. Similarly, the flow region 184 may be configured as a fine flow adjustment region that corresponds to travel range 194 of the roller wheel 130. Also, the flow region 186 may be configured as a closing region that corresponds to travel range 196 of the roller wheel 130.

Accordingly, in aspects of the disclosure, during manufacturing of the precision roller clamp assembly 100, the flow region 182 may be configured or tuned to decrease the fluid flow rate from full open flow to a clinically relevant and controlled high flow rate (e.g., 250 mL/hr), the flow region 184 may be configured or tuned to decrease the fluid flow rate from a clinically relevant and controlled high flow rate to a controlled low flow rate (e.g., 250 mL/hr to 25 m/L hr), and the flow region 186 may be configured or tuned to decrease the fluid flow rate from a controlled low flow rate to a full fluid stop (e.g., 25 mL/hr to 0 m/L hr). Thus, any one of the width W or depth D of the tube groove 133 and the gap distance GD may be designed to manufacture a precision roller clamp assembly 100 with the desired flow profile 180.

In aspects of the disclosure, the precision roller clamp assembly 100 may cause complete flow stoppage when the roller wheel 130 is positioned at the second housing end 109. For example, the roller wheel 130 is able to occlude flow during pressure spikes (e.g., during a syringe push) when the roller wheel 130 is so positioned. Further, the position of the roller wheel 130 at the far end of the movement range 190 closest to the second housing end 109 provides an easy and instant visual notice to a clinician or other user that the flow rate is stopped.

In aspects of the disclosure, the precision roller clamp assembly 100 provides a low and user friendly actuation force (e.g., ≤20 newtons (N)). For example, the large travel range 194 of the roller wheel 130 for the clinically relevant flow rate range between 250 mL/hr and 25 mL/hr provides a long travel path for smooth and easy actuation of the roller wheel 130.

In aspects of the disclosure, the precision roller clamp assembly 100 provides flow stability at any given position of the roller wheel 130. For example, the tube 24 is appropriately constrained between the roller wheel 130 and the tube groove 133 over the entirety of the movement range 190, so that when the tube 24 undergoes stress relaxation an inner diameter of the tube 24 can only decrease into itself, resulting in only a possible negative flow rate change and not an unintended positive flow rate change. Here, the fine adjustment parameters over such a large portion of the movement range 190 also avoids large differentials between flow rates of adjacent positions.

Figure 12:
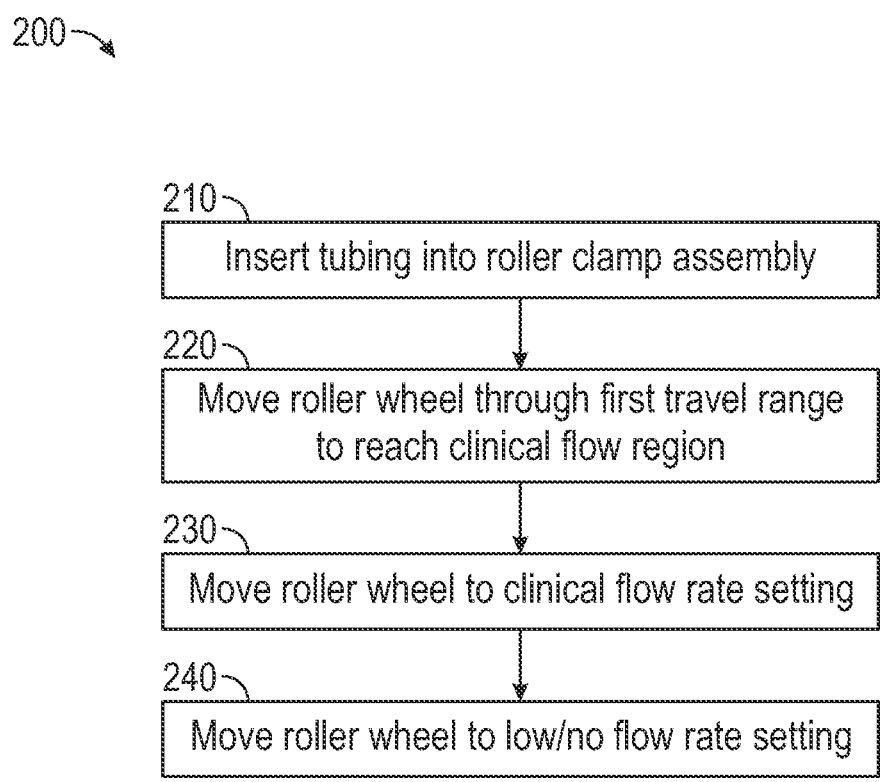
FIG. 12 depicts a method of operating a precision roller clamp assembly, according to aspects of the disclosure.

With reference to FIG. 12, a method 200 of operating a precision roller clamp assembly is provided. In step 210, tubing (e.g., IV tube 24) is placed or disposed in a precision roller clamp assembly 100. For example, tube 24 may be inserted into housing 105 with the roller wheel 130 in a wide open position closest to the first housing end 107 (e.g., minimally contacting or impinging the tube 24).

In step 220, the roller wheel 130 may be moved through the travel range 192 to the beginning of the travel range 194 to engage and impinge the tube 24. For example, the roller wheel 130 may be moved from the first housing end 107 of the housing 105 towards the second housing end 109 of the housing 105, so that a narrowing between any of the guide wall 112 and the roller 130 (e.g., the gap depth GD), the width W of the tube groove 133, and the depth D of the tube groove causes the roller wheel 130 to compress or squeeze the contacted portion of the tube 24. This compression causes the fluid flow rate in the tube 24 to change from a full open flow rate in the full open flow region 182 to a high controlled clinical flow rate (e.g., from full open to 250 ml/hr), which is the beginning of the clinical flow range in the fine flow adjustment flow region 184.

In step 230, the roller wheel 130 may be moved to any portion of the travel range 194 to further impinge the tube 24. For example, the roller wheel 130 may be moved from the start of the travel range 194 to anywhere up to and including the end of the travel range 194 closest to the second housing end 109, so that a narrowing between any of the guide wall 112 and the roller 130 (e.g., the gap depth GD), the width W of the tube groove 133, and the depth D of the tube groove causes the roller wheel 130 to correspondingly compress or squeeze the contacted portion of the tube 24, thus causing the fluid flow rate in the tube 24 to change from the high controlled clinical flow rate to any desired clinical flow rate down to and including the low controlled clinical flow rate (e.g., from 250 ml/hr to 25 ml/hr).

In step 240, the roller wheel 130 may be moved from the travel range 194 to any portion of the travel range 196 to further impinge the tube 24. For example, the roller wheel 130 may be moved from the travel range 194 to anywhere up to and including the end of the travel range 196 closest to the second housing end 109, so that a narrowing between any of the guide wall 112 and the roller 130 (e.g., the gap depth GD), the width W of the tube groove 133, and the depth D of the tube groove causes the roller wheel 130 to correspondingly compress or squeeze the contacted portion of the tubing 24, thus causing the fluid flow rate in the tubing 24 to change from the selected clinical flow rate in the fine flow adjustment flow region 184 to any desired low or no flow rate (e.g., from 25 ml/hr to 0 ml/hr) in the closing flow region 186.

In one or more embodiments of the disclosure, a roller clamp assembly comprises a housing configured to receive a portion of a tube of an infusion set, the housing comprising: two opposing side walls spaced apart from each other, each side wall having an opposing guide groove longitudinally positioned in an interior surface; a guide wall disposed between the side walls; and a tube groove disposed within the guide wall; and a roller wheel having two axial projections slidingly seated in the guide grooves, the roller configured to move along a longitudinal axis of the housing over a movement range as the projections slide in the guide grooves.

In aspects of the disclosure, a width of the tube groove is varied over a length of the tube groove. In aspects of the disclosure, a depth of the tube groove is varied over a length of the tube groove. In aspects of the disclosure, a gap between a perimeter of the roller wheel and the guide wall is varied over a length of the tube groove. In aspects of the disclosure, the movement range comprises a first travel range starting at a first end of the housing, wherein a first end of the first travel range is configured to provide a fully open flow rate of fluid through the tube and a second end of the first travel range is configured to provide a determined high flow rate of fluid through the tube. In aspects of the disclosure, the determined high flow rate is 250 mL/hr. In aspects of the disclosure, the first travel range comprises less than or equal to 25 percent of the movement range.

In aspects of the disclosure, the movement range comprises a second travel range starting at the second end of the first travel range, wherein a first end of the second travel range is configured to provide the determined high flow rate of fluid through the tube and a second end of the second travel range is configured to provide a determined low flow rate of fluid through the tube. In aspects of the disclosure, the determined low flow rate is 250 mL/hr. In aspects of the disclosure, the second travel range comprises greater than or equal to 50 percent of the movement range.

In aspects of the disclosure, the movement range comprises a third travel range starting at the second end of the second travel range, wherein a first end of the third travel range is configured to provide the determined low flow rate of fluid through the tube and a second end of the third travel range is configured to provide a fully closed flow rate of fluid through the tube. In aspects of the disclosure, the fully closed flow rate is 0 mL/hr. In aspects of the disclosure, the third travel range comprises less than or equal to 25 percent of the movement range. In aspects of the disclosure, the third travel range ends at a second end of the housing.

In aspects of the disclosure, the roller clamp assembly is configured to have a flow profile comprising a first flow region that corresponds to the first travel range, a second flow region that corresponds to the second travel range and a third flow region that corresponds to the third travel range. In aspects of the disclosure, one or more of a width of the groove, a depth of the groove and a gap between a perimeter of the roller wheel and the guide wall are configured to create a desired flow profile. In aspects of the disclosure, one or more of a width of the groove, a depth of the groove and a gap between a perimeter of the roller wheel and the guide wall are configured to create one of a desired first flow region, a desired second flow region and a desired third flow region. In aspects of the disclosure, the movement range is configured for operation of the roller wheel by an actuation force less than or equal to 20 newtons.

In one or more embodiments of the disclosure, a method of operating a roller clamp assembly comprises inserting a tube of an infusion set into a precision roller clamp assembly comprising a housing having two opposing side walls spaced apart from each other, each side wall having an opposing guide groove longitudinally positioned in an interior surface, a guide wall disposed between the side walls and a tube groove disposed within the guide wall, and a roller wheel having two axial projections slidingly seated in the guide grooves; moving the roller wheel through a first travel range of the guide groove to engage the tube to cause a flow rate of fluid through the tube to go from a fully open flow rate to a clinically determined high flow rate; and moving the roller wheel to a position in a second travel range of the guide groove to increasingly impinge the tube to cause a desired flow rate of fluid through the tube between the clinically determined high flow rate and a clinically determined low flow rate.

In aspects of the disclosure, the method further comprises moving the roller wheel to a position in a third travel range of the guide groove to further impinge the tube to cause a desired flow rate of fluid through the tube between the clinically determined low flow rate and no flow rate.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A roller clamp assembly comprising: a housing configured to receive a portion of a tube of an infusion set, the housing comprising: two opposing side walls spaced apart from each other, each side wall having an opposing guide groove longitudinally positioned in an interior surface; a guide wall disposed between the side walls; and a tube groove disposed within the guide wall; one or more protrusions disposed on an inner surface of the guide wall adjacent each side of the tube groove; and a roller wheel having two axial projections slidingly seated in the guide grooves, the roller configured to move along a longitudinal axis of the housing over a movement range as the projections slide in the guide grooves, wherein a width of the tube groove is varied over a length of the tube groove along a length of the housing, wherein a first end of the tube groove has a first width of zero and a second end of the tube groove has a second width of zero, wherein the movement range comprises a first travel range starting at a first end of the housing, wherein a first end of the first travel range is configured to provide a first fully open flow rate of fluid through the tube and a second end of the first travel range is configured to provide a determined second flow rate of fluid through the tube, wherein the determined second flow rate is less than the first fully open flow rate, wherein the width of the tube groove over the first travel range has a third width greater than zero at the first end of the first travel range that widens to a fourth width greater than the third width within the first travel range and maintains the fourth width to the second end of the first travel range, wherein the movement range comprises a second travel range starting at the second end of the first travel range, wherein a first end of the second travel range is configured to provide the determined second flow rate of fluid through the tube and a second end of the second travel range is configured to provide a determined third flow rate of fluid through the tube, wherein the determined third flow rate is less than the determined second flow rate, wherein the movement range comprises a third travel range starting at the second end of the second travel range, wherein a first end of the third travel range is configured to provide the determined third flow rate of fluid through the tube and a second end of the third travel range is configured to provide a fourth fully closed flow rate of fluid through the tube, and wherein the first travel range comprises less than or equal to 25 percent of the movement range, the second travel range comprises greater than or equal to 50 percent of the movement range and the third travel range comprises less than or equal to 25 percent of the movement range.

2. The roller clamp assembly of claim 1, wherein a depth of the tube groove is varied over a length of the tube groove.

3. The roller clamp assembly of claim 1, wherein a gap between a perimeter of the roller wheel and the guide wall is varied over a length of the tube groove.

4. The roller clamp assembly of claim 1, wherein the determined second flow rate is 250 mL/hr.

5. The roller clamp assembly of claim 1, wherein the determined third flow rate is 250 mL/hr.

6. The roller clamp assembly of claim 1, wherein the fourth fully closed flow rate is 0 mL/hr.

7. The roller clamp assembly of claim 1, wherein the third travel range ends at a second end of the housing.

8. The roller clamp assembly of claim 1, wherein the roller clamp assembly is configured to have a flow profile comprising a first flow region that corresponds to the first travel range, a second flow region that corresponds to the second travel range and a third flow region that corresponds to the third travel range.

9. The roller clamp assembly of claim 8, wherein one or more of a width of the groove, a depth of the groove and a gap between a perimeter of the roller wheel and the guide wall are configured to create a desired flow profile.

10. The roller clamp assembly of claim 8, wherein one or more of a width of the groove, a depth of the groove and a gap between a perimeter of the roller wheel and the guide wall are configured to create one of a desired first flow region, a desired second flow region and a desired third flow region.

11. The roller clamp assembly of claim 1, wherein the movement range is configured for operation of the roller wheel by an actuation force less than or equal to 20 newtons.

12. The roller clamp assembly of claim 1, wherein the one or more protrusions disposed on the inner surface of the guide wall extend toward the roller wheel.

13. A method of operating the roller clamp assembly of claim 1, the method comprising:
inserting the tube of an infusion set into the roller clamp assembly
moving the roller wheel through the first travel range of the guide groove to engage the tube to cause the flow rate of fluid through the tube to go from the first fully open flow rate to the determined second flow rate; and
moving the roller wheel to a position in the second travel range of the guide groove to increasingly impinge the tube to cause a desired flow rate of fluid through the tube between the determined second flow rate and the determined third flow rate that is less than the determined second flow rate.

14. The method of claim 13, further comprising;
moving the roller wheel to a position in the third travel range of the guide groove to further impinge the tube to cause a desired flow rate of fluid through the tube between the determined third flow rate and no flow rate.

* * * * *